United States Patent [19]
Morris et al.

[11] Patent Number: 5,325,853
[45] Date of Patent: Jul. 5, 1994

[54] CALIBRATION MEDIUM CONTAINMENT SYSTEM

[75] Inventors: Russell L. Morris, St. Paul; David W. Deetz, North Oaks, both of Minn.

[73] Assignee: Diametrics Medical, Inc., Roseville, Minn.

[21] Appl. No.: 940,271

[22] Filed: Sep. 2, 1992

[51] Int. Cl.$^5$ ............................................. A61B 5/05
[52] U.S. Cl. .................................. 128/630; 128/635; 204/403
[58] Field of Search ............... 128/630, 632, 635, 637, 128/760, 912; 204/403, 415, 416, 418, 419, 153.17

[56] References Cited

U.S. PATENT DOCUMENTS

| | | | |
|---|---|---|---|
| 4,180,771 | 12/1979 | Guckel | 128/635 |
| 4,218,298 | 8/1980 | Shimada et al. | 128/635 |
| 4,535,786 | 8/1985 | Kater | 128/630 |
| 4,734,184 | 3/1988 | Burleigh et al. | 204/415 |
| 4,786,394 | 11/1988 | Enzer et al. | 204/403 |
| 5,046,496 | 9/1991 | Betts et al. | 128/635 |
| 5,089,421 | 2/1992 | Dieffenbach | 128/635 |
| 5,096,669 | 3/1992 | Lauks et al. | 204/403 |
| 5,098,545 | 3/1992 | Patko | 204/416 |
| 5,165,406 | 11/1992 | Wong | 128/760 |

FOREIGN PATENT DOCUMENTS 282349 9/1988 European Pat. Off. .

OTHER PUBLICATIONS

Opdycke, Walter N., and M. E. Meyerhoff, "Development and Analytical Performance of Tubular Polymer Membrane Electrode Based Carbon Dioxide Catheters", Anal. Chem., 1986, vol. 58, pp. 950–956.

*Primary Examiner*—Lee S. Cohen
*Assistant Examiner*—Samuel Gilbert
*Attorney, Agent, or Firm*—Haugen and Nikolai

[57] ABSTRACT

A method and apparatus which contemplates coverage control, and collateral containment of calibration media with respect to diverse electrodes in a flow-through calibration and measurement cell during storage and sensor calibration and in which the calibration media are displaced by the entry of a subsequent sample to be tested. The system is associated with a disposable cartridge insertable into a portable instrument that contains all of the electronics and other end support equipment associated with automated calibration and sample measurement.

17 Claims, 1 Drawing Sheet

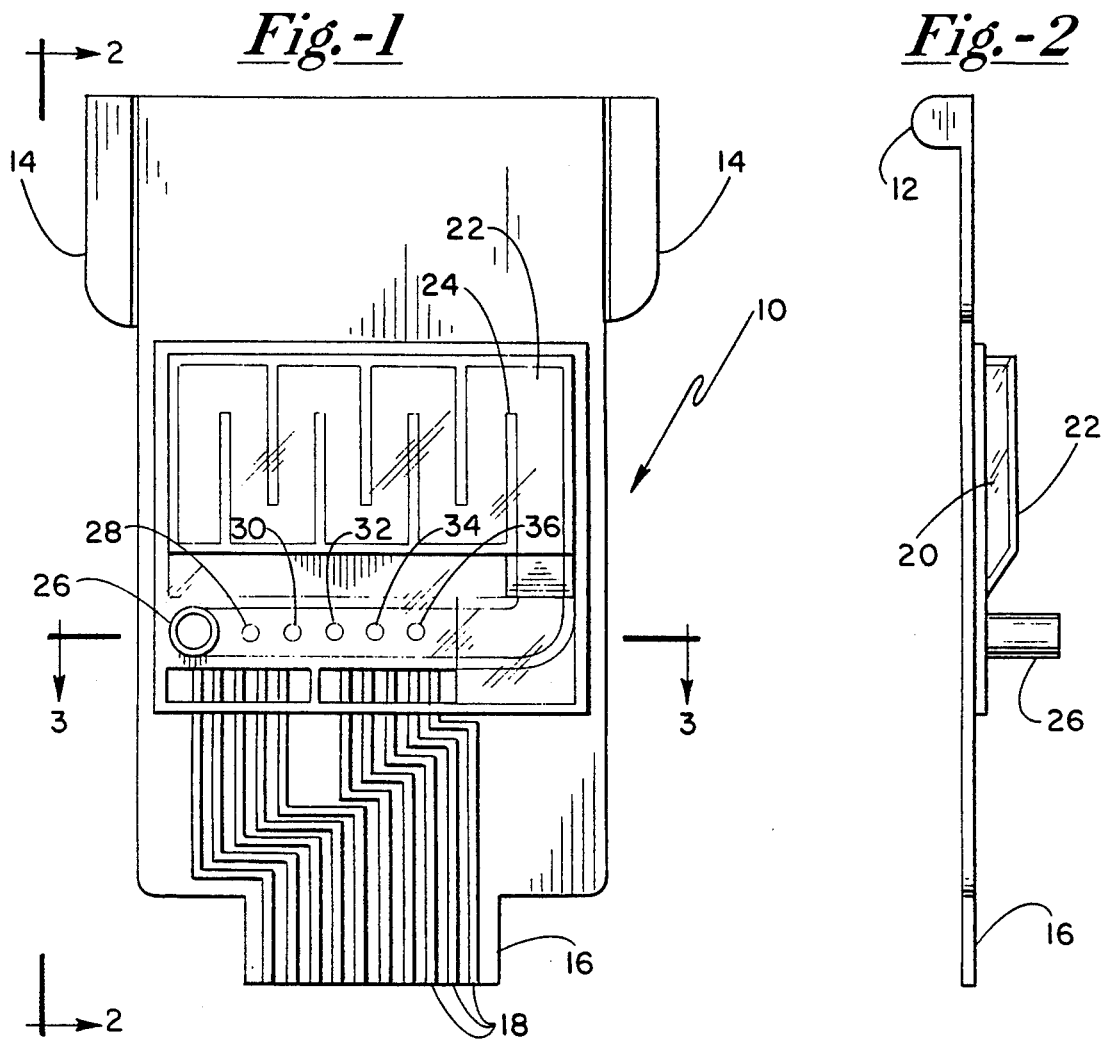
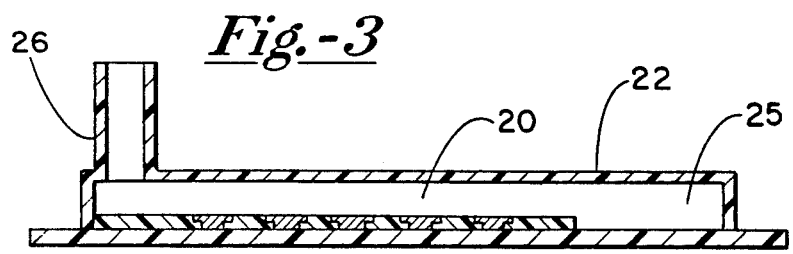
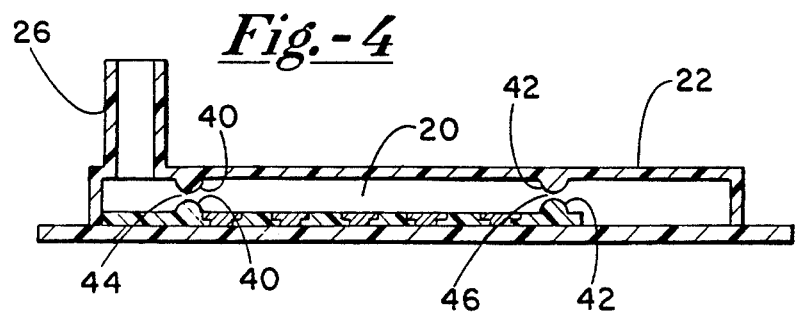

CALIBRATION MEDIUM CONTAINMENT SYSTEM

BACKGROUND OF THE INVENTION

I. Field of the Invention

The present invention is directed generally to a self-contained, disposable cartridge-type electrochemical test cell for use with an associated test instrument having an integral temperature stabilized autogenous electrode calibration and measurement system and, more particularly, to a method and system for controlling and stabilizing the location of the calibration material with respect to the electrode system so that calibration can be accomplished automatically and thereafter displacement of the calibration medium by the sample readily accommodated.

II. Description of the Related Art

The field of diagnostic medicine is fast becoming more sophisticated and complex. The ability to make rapid or immediate diagnostic determinations characteristic of the current condition of a patient so that the proper emergency steps may be taken in a timely manner to improve or stabilize the condition of the patient, for example, during surgery or during the treatment of traumatic injury has become very important. Blood gas determinations including the partial pressures of oxygen ($PO_2$), carbon dioxide ($PCO_2$), acidity or alkalinity (pH) and concentration of certain electrolyte species such as potassium ($K^+$) in the blood are examples of extremely important instantaneous indications of respiratory deficiency, efficiency of inhalation therapy, renal function and other vital bodily processes.

Blood gas determinations heretofore have been made utilizing stationary clinical laboratory instruments that have large reference electrodes and pH, $CO_2$ and $O_2$ electrodes. The instruments must be periodically calibrated using a calibration system which is cumbersome in size and intended for use only at a specific temperature. Operation of the instrument is also generally restricted to a specific known temperature, e.g., 37° C. The reference and pH electrodes must be calibrated using a liquid system. The $CO_2$ and $O_2$ electrodes can be calibrated using either a liquid medium or a calibration gas. In addition to periodic recalibration of the instrument, control samples also need to be analyzed to ensure continued proper operation; these samples also have restrictive temperature ranges for use. The specific composition of typical liquid control or calibration fluid systems is such that the reference or known equilibrium partial pressures of oxygen and carbon dioxide are temperature dependent and so occur only at the specific storage temperature. Operating or using a liquid-based calibration system at a temperature other than the designed temperature may introduce a decided amount of error into the readings. Gaseous $CO_2$ and $O_2$ may also be used to calibrate $CO_2$ and $O_2$ sensors in such instruments, but that requires the need for obtaining and for storage of cylinders of compressed gases.

A calibration and measurement system which is small and portable and that makes use of a calibration system that is temperature independent would be very desirable. Reducing the temperature dependence of the calibration system as by temperature stabilization of the amount of contained dissolved or dissociated gaseous species of interest in media for a variety of applications has been demonstrated.

In this regard, it has been found possible to create a packaged system that provides a stable concentration of a gas in a calibration medium despite changes in the temperature of the calibration medium or solvent within a reasonable range of ambient temperature. Such a system is illustrated and described in copending application Ser. No. 07/806,495 of David W. Deetz and Russell L. Morris, filed Dec. 13, 1991 and assigned to the same assignee as the present invention. To the extent necessary for an understanding of the present application, material from that application may be deemed incorporated by reference herein. That temperature-independent system involves the use of an additional separate, reversible equilibrium compensating source containing an amount of the gas or gases of interest packaged along with the calibration medium. The additional source known as a "reservoir" acts in the manner of a buffer to control changes in the partial pressure of the gas or gases of interest in the atmosphere of the package including the atmosphere contacting the calibration liquid. The changes in partial pressure can be tailored to compensate for changes in the solubility of the gas or gases of interest in the calibration medium over a designed range. The system can also be used to control change in the partial pressure of a species of interest as a function of temperature change.

Both the calibration medium and the reservoir are contained in separate gas-permeable enclosures within an outer, common enclosure such that gaseous species may be readily exchanged with respect to the common atmosphere of the sealed outer enclosure but such that the media themselves do not contact each other. The reservoir equilibrium is designed to have a more sensitive temperature dependence and the enclosure of the reservoir to be more permeable to the gas(es) of interest than those of the calibration system and container in order that the reservoir system react more quickly to temperature changes and thus to dominate changes produced in the calibration container. Temperature changes which produce an increase or decrease in the partial pressure of a species of interest in the reservoir medium will cause a corresponding increase or decrease in the partial pressure of that species in the common atmosphere at a rate that will, in turn, anticipate and compensate changes in the calibration system material.

For example, the reservoir medium is designed, upon heating, to expel amounts of a gas or gases into the package atmosphere anticipating the reaction of the sample by raising the partial pressures of these gases in the common atmosphere at a somewhat faster rate than they would be lost from the calibration medium, thereby preempting the thermodynamic driving force for the gases to leave through the permeable shell of the calibration container. Conversely, if the system cools and the solubility of the gases of interest in the calibration medium increases, the reservoir acts to reverse the phenomena of the heating mode and reabsorbs the gas or gases into the reservoir medium from the package atmosphere at a somewhat faster rate than the reabsorption in the calibration medium thereby lowering the partial pressure of the gas or gases of interest in the common atmosphere to eliminate any driving force for the gas or gases of interest in the common atmosphere to permeate the calibration enclosure and dissolve in the calibration medium. This preserves the resulting concentration of each such species of interest in the calibration medium regardless of the direction of temperature change within a designed limited ambient temperature range.

Typically, the calibration medium and/or the reservoir medium are solutions of selective solvents with or without complexing agents or buffers. In the case where $CO_2$ is the species of interest, both the reservoir and the sample media may be aqueous solutions of $CO_2$. A system where the sample pH is 7.4 and the reservoir is buffered to a pH of 8.6, for example, exhibits good temperature/concentration or ($pCO_2$) stability in the 20° C. to 30° C. range; but ($pCO_2$) is quite temperature dependent for a reservoir pH above 9.0, or below 8.2.

It being further recognized that while the copending cross-referenced application addresses the physics and chemistry of temperature related calibration media composition stabilization and control, it remains necessary to stabilize and control the locus of the calibration media materials themselves with respect to the sensor electrode system to achieve proper electrode function and automate calibration. In this regard, it is desirable that the calibration medium or media be stored or available over one or more of the electrodes as required for automatic calibration. In addition, the calibration materials must be readily displaceable for the subsequent sample to be subjected to analysis just after calibration so that the sample and calibration media do not interfere with each other.

Accordingly, it is a primary object of the present invention to provide a disposable, self-contained automated calibration and sample testing enclosure that stabilizes the calibration material in contact with selected electrodes until calibration is concluded, yet allows easy displacement by the sample solution to be analyzed.

Another object is to provide a calibration media of a consistency commensurate with maintaining a desired location during storage and through calibration.

A further object of the present invention is the provision of flow control and storage volumes for used displaced calibration fluid.

A still further object contemplates a containment system that maintains calibration material over sensors in a disposable test cartridge used for measuring blood gases and pH, as well as other analyses.

An additional object of the invention is to provide a containment system that maintains calibration fluid over the sensors of a disposable test cartridge by the provision of a flow cell region over the sensors with flanking constrictions sufficient to contain an aqueous or other calibration fluid, yet large enough to allow blood flow.

Yet an additional object contemplates a containment system that maintains calibration material over sensors in a disposable test cartridge used for measuring blood gases and pH using both aqueous and non-aqueous calibration material solvents.

Yet still another object contemplates a containment system that maintains calibration material over sensors in a disposable test cartridge used for measuring blood gases and pH using a gel stabilized dispersion of aqueous and/or non-aqueous calibration materials.

These and other objects will become apparent to those skilled in the art who persevere through this specification in light of the drawings and claims.

SUMMARY OF THE INVENTION

The present invention involves a self-contained, disposable cartridge system including a flow-through cell containing the sensors used for blood gas analysis including pH, $pCO_2$, $pO_2$ and possibly $K^+$ sensors, in a configuration in which the blood gas analysis is designed to be carried out after automatic calibration of the sensor electrodes. The disposable cartridge is designed to be inserted into an instrument that contains all of the electronics and other support equipment to accomplish the calibration and measurement using the electrode system contained in the disposable cartridge. The disposable cartridge, then, is designed to contain a system which automatically calibrates the electrodes after the cartridge is inserted in and engaged in conjunction with the operation of the portable instrument. Combinations of calibration media and disposable cartridge electrode and media containment and storage design are contemplated such that the calibration material is contained over the sensors as required in the flow-through cell chamber during storage and shipment and up to the time of calibration but is thereafter readily displaced by the injection of the sample of interest, normally blood.

It is contemplated with respect to the present invention that the media supporting calibration may take a variety of forms. These include highly fluid aqueous solutions; highly fluid non-aqueous solutions, which may or may not be miscible with aqueous media may be used. Variations in the viscosity of the media are clearly also contemplated. Gels or even solids exhibiting the properties required with respect to taking on and giving up the species necessary for accurate calibration may be employed. A gel stabilized dispersion of aqueous and/or non-aqueous calibration material may also be used. The gel may be based on natural materials such as agar, collagen, agarose, other natural polysaccharide materials or any of numerous compatible synthetic polymer based materials. An amount of surfactant may be used to enhance the temperature and/or time stability of the dispersion if required.

The environment of calibration, and hence that of sample determination, is that of a disposable cartridge unit having a plurality of electrochemical electrode sensors to perform each contemplated function. One embodiment contains sensors for determining $CO_2$, $O_2$, pH and $K^+$ together with a reference electrode. These are contained in a hollow flow-through cell channel or chamber within the disposable cartridge. Provision is made to maintain the presence of the calibration material over the required some or all of the electrodes during shipment, storage and calibration. The system may take any one of several configurations depending on the combination of electrodes and calibration materials contemplated. For example, the calibration material may need to allow ionic conduction between the pH and reference electrodes or between the $CO_2$ and pH and the reference electrode in certain configurations. The oxygen electrode, on the other hand, may be designed to operate with a specific in situ calibration material or may be calibrated to atmospheric oxygen using only a wetting medium to support ionic conduction.

The containment means itself may take one of several forms. If the use of an aqueous or non-aqueous calibration fluid that is of low viscosity be contemplated, the flow-through cell channel or chamber region including the sensors is provided with constrictions on each end sufficient to contain the fluid based on surface tension, yet large enough to allow blood flow. If, on the other hand, a gel stabilized or highly viscous system be used, physical members for flow restriction may not be required.

The disposable cartridge contemplated by the invention consists of an inlet port addressing the flow-through cell, passage or sample chamber having a cell volume and which carries the electrodes in communication with the interior thereof. This chamber also is designed to retain the calibration medium or media prior to injection or insertion of the sample. The cartridge further includes an outlet passage, exit or egress flow path in fluid flow communication with the sample chamber and with a used calibration fluid disposal chamber such that the insertion or injection of the fluid sample into the sample chamber displaces the calibration medium from the sample chamber into the used calibration fluid storage chamber to prevent interference with sample measurement.

As a physical medium, a calibration material having multiple phases including aqueous and non-aqueous phases may also be used. Likewise, a gel system may be designed to melt at a temperature close to body temperature such that it is either liquified at operating temperature or gelled in a manner such that it may be displaced by the blood sample as a solid or plug. Solids may include high average molecular weight polymers or other materials which reversibly transceive the species of interest. Of course, an aqueous or non-aqueous gel may also be used.

BRIEF DESCRIPTION OF THE DRAWINGS

In the drawings, wherein like numerals are utilized to designate like parts throughout the same:

FIG. 1 is a top plan view of a disposable cartridge usable with the present invention;

FIG. 2 is a left-side elevational view of the cartridge of FIG. 1 as designated by lines 2—2 in FIG. 1;

FIG. 3 is a sectional end elevational view taken along lines 3—3 of FIG. 1; and

FIG. 4 depicts an alternate internal embodiment configuration to that illustrated in FIG. 3 employing spaced flow constrictors.

DETAILED DESCRIPTION

As is evident from the summary above, the electrode array and so the calibration media associated with the disposable cartridge of the present invention may take any of many forms and the description of the detailed embodiments herein are decidedly intended by way of example rather than limitation. Accordingly, there is shown in FIG. 1 generally at 10 a disposable cartridge unit that is designed to be inserted into an instrument (not shown) that contains the power supply for and all of the electronics and other support equipment to utilize the cartridge of the invention in the manner intended, yet which itself does not form a part of this invention. This includes means to calibrate all of the electrodes and, upon the insertion of a sample, make all the measurement determinations with respect to that sample. The cartridge 10 is intended to be employed as a disposable on a one-time basis which includes insertion, automatic calibration and sample measurement by the associated instrument.

The disposable cartridge 10 is constructed of a polymer material such as polycarbonate and includes an integral handle 12 provided to grasp the cartridge and guide members 14 which aid the insertion of end 16 into the corresponding associated portable diagnostic instrument (not shown). The cartridge is provided with an array of functional electrical conductors as at 18 which provide the required cartridge/instrument interconnect including all necessary input and output conductors. The conductors may be constructed in any well-known manner. They may be deposited on the surface of the polymeric material utilizing thick or thin film technology or any other appropriate technique as many such are readily available to those skilled in the art. The cartridge unit itself contemplates a plurality of internal passages or chambers including a calibration and measurement flow-through cell chamber 20 and a used calibration medium and excess sample storage chamber 22 which may have a plurality of partitions 24 thereby defining a tortuous maze. The compartment 22 is connected with the electrode-containing measurement compartment 20 via a fluid passage 25. The system also includes a sample inlet port at 26 and a plurality of sensor electrodes including a reference electrode 28, pH electrode 30, $CO_2$ electrode 32, potassium ($K^+$) electrode 34 and $O_2$ electrode 36. The electrode arrangement in the system, of course, may vary with application.

FIG. 4 depicts an embodiment similar to that of FIG. 3 except that the ingress and egress to the compartment 20 is further limited by pairs of flanking, oppositely disposed flow restriction devices as at 40 and 42. These devices are designed to permit flow through the openings 44 and 46 only upon the application of an external force such as that which could be provided by a syringe. This enables the system to contain even low viscosity aqueous calibration solutions during storage and through calibration by relying on surface tension for retention. Forcible injection or insertion of a blood or other fluid sample into port 26 will readily displace the calibration media from the volume 20 into the volume 22, through openings 44 and 46.

The system of the present invention contemplates a method of providing an automated calibration system for a disposable cartridge of the class described in addition to the apparatus itself. The method includes providing means commensurate with the composition and viscosity of the calibration medium or media to provide proper containment during storage and calibration which is then receptive to displacement by the in-flow of the sample solution which thereby then makes use of the same electrochemical sensor system.

The system of the present invention, as introduced above, contemplates calibration materials of several forms. In this manner, a non-aqueous phase may be sandwiched between two aqueous phases with one of the aqueous phases placed over the pH, $CO_2$ and reference electrodes and the non-aqueous phase over the $O_2$ sensor, it being recognized that the electrodes of the system can be placed in any desired order and they are suitably connected through he conductors as at 18 to the instrument upon the insertion of the disposable cartridge 10. For example, if the $O_2$ sensor is designed for use with a perfluorocarbon non-aqueous calibration phase, the aqueous phases might be placed at each end to contain the low surface-tension, non-aqueous perfluorocarbon phase in the embodiment of FIG. 4. The flow-through channel 20 must be small enough, however, to prevent the phases from moving relative to one another during shipping and handling.

With respect to gel systems, a gel stabilized dispersion or solution of aqueous and/or non-aqueous calibration material can be employed in which the gel is a natural material such as agar, agarose, collagen or any suitable polysaccharide, the gel can also be based on one or more synthetic polymers such as polyvinyl alcohol (PVA), polyvinyl pyrrolidone (PVP) or the like. An amount of surfactant may be used to enhance the temperature and time stability of a dispersion. The gel system may be signed to melt at a temperature slightly below 37° C. so that it is in liquid form at body temperature which is normally the contemplated operating temperature of the sample determination system of the instrument. The gel system may be designed to melt at a temperature higher than 37° C. so that it is displaced by the blood or other sample as a solid or plug which can be squeezed from the electrode chamber into the used calibration fluid chamber as a solid. The gel or other electrolyte calibration systems can be utilized with a subset of sensors that contains materials and/or salts necessary to calibrate the sensors over which it is placed.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself. For example, the cartridge system described may also be used with other types of chemical sensors. These include optical sensor systems.

What is claimed is:

1. A self-contained self-calibrating disposable cartridge for the analysis of liquid samples insertable for use with an associated diagnostic instrument comprising:
    (a) an enclosure containing a dual-function chamber for calibration media storage and fluid sample analysis, said dual-function chamber defining a hollow interior and inlet and outlet accesses;
    (b) an array of electrochemical sensors including sensor electrodes in communication with the interior of the dual-function chamber;
    (c) an amount of at least one compatible calibration material for one or more of the electrochemical sensors predisposed and stored in the dual-function chamber in contact with said one or more of the electrochemical sensors for immediate availability for the cailbration thereof, said calibration material further being of a type displaced by the introduction of a liquid sample to be analyzed to prevent cross-contamination; and
    (d) a plurality of conductors connected to the sensor electrodes for connecting the sensor electrodes to calibration and analysis devices outside the cartridge.

2. The cartridge of claim 1, wherein the calibration material is selected from a group consisting of gels and stabilized dispersions of calibration materials.

3. The cartridge of claim 2 wherein the calibration material is applied to one or more of the sensors in film form.

4. The cartridge of claim 1 further comprising flow restriction means in the inlet and outlet accesses of the dual-function chamber to prevent loss of the calibration material from the chamber prior to displacement by a liquid sample.

5. The cartridge of claim 4 wherein the calibration material is a viscous liquid.

6. A self-contained self-calibrating disposable cartridge for the analysis of liquid samples insertable for use with an associated diagnostic instrument comprising:
    (a) an enclosure containing a dual-function chamber for calibration media storage and fluid sample analysis, said dual-function chamber defining a hollow interior and inlet and outlet accesses;
    (b) an array of electrochemical sensors including sensor electrodes in communication with the interior of the dual-function chamber;
    (c) an amount of at least one compatible calibration material for one or more of the electrochemical sensors predisposed and stored in the dual-function chamber in contact with said one or more of the electrochemical sensors for immediate availability for the calibration thereof, said calibration material further being of a type displaced by the introduction of a liquid sample to be analyzed to prevent cross-contamination;
    (d) a plurality of conductors connected to the sensor electrodes for connecting the sensor electrodes to calibration and analysis devices outside the cartridge;
    (e) enclosed hollow waste chamber in flow passage communication with the outlet access of the dual-function chamber and having sufficient capacity to contain displaced calibration material and excess sample material; and
    (f) sample access port for receiving a liquid sample to be analyzed in the dual-function chamber in fluid passage communication with the inlet access of the dual-function chamber.

7. The cartridge of claim 6 wherein the calibration material is selected from a group consisting of gels and stabilized dispersions of calibration materials.

8. The cartridge of claim 7 wherein the calibration material is applied to one or more of the sensors in film form.

9. The cartridge of claim 7 wherein the selected gel is a liquid at normal operating temperature.

10. The cartridge of claim 7 wherein the electrochemical sensors include at least reference, pH, $CO_2$ and $O_2$ electrodes.

11. The cartridge of claim 7 wherein the electrodes include a $K^+$ electrode.

12. The cartridge of claim 11 wherein the calibration materials are selected from the group consisting of gels and stabilized dispersions of calibration materials.

13. The cartridge of claim 6 further comprising flow restriction means in the inlet and outlet accesses of the dual-function chamber to prevent loss of the calibration material from the chamber prior to displacement by a liquid sample.

14. The cartridge of claim 13 wherein the calibration material is a viscous liquid.

15. A self-contained self-calibrating disposable cartridge for the analysis of liquid samples insertable for use with an associated diagnostic instrument comprising:
    (a) an enclosure containing a dual-function chamber for calibration media storage and fluid sample analysis, said dual-function chamber defining a hollow interior and inlet and outlet accesses;
    (b) an array of electrochemical sensors including sensor electrodes in communication with the interior of the dual-function chamber;
    (c) an amount of a plurality of compatible calibration materials for one or more of the electrochemical sensors predisposed and stored in the dual-function chamber each calibration material being in contact with one or more of the electrochemical sensors for immediate availability for the calibration thereof; and (d) enclosed hollow waste chamber in flow passage communication with the outlet access of the dual-function chamber and having sufficient capacity to contain the calibration material and excess sample material;

(e) sample access port for receiving a liquid sample to be analyzed in the dual-function chamber in fluid passage communication with the inlet access of the dual-function chamber;

(f) wherein the introduction of a liquid sample into the dual function chamber produces displacement of the calibration materials to the hollow waste chamber such that the liquid sample material replaces the calibration material as material in contact with the electrochemical sensors in the dual-function chamber; and (g) a plurality of conductors connected to the sensor electrodes for connecting the sensor electrodes to calibration and analysis devices outside the cartridge.

16. The cartridge of claim 15 wherein at least one of the calibration materials is a viscous liquid.

17. The cartridge of claim 16 further comprising flow restriction means in the inlet and outlet accesses of the dual-function chamber to prevent loss of the calibration material from the chamber prior to displacement by a liquid sample.

* * * * *